US009149330B2

(12) United States Patent
Sharareh et al.

(10) Patent No.: US 9,149,330 B2
(45) Date of Patent: *Oct. 6, 2015

(54) CATHETER WITH OMNI-DIRECTIONAL OPTICAL LESION EVALUATION

(71) Applicant: BIOSENSE WEBSTER, INC., Diamond Bar, CA (US)

(72) Inventors: Shiva Sharareh, Laguna Niguel, CA (US); Chad Allen Lieber, Rolla, MO (US); Jeffrey William Schultz, Chino, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/137,590

(22) Filed: Dec. 20, 2013

(65) Prior Publication Data

US 2014/0350547 A1    Nov. 27, 2014

Related U.S. Application Data

(63) Continuation of application No. 11/417,092, filed on May 2, 2006, now Pat. No. 8,628,520.

(51) Int. Cl.
*A61B 18/14* (2006.01)
*A61B 19/00* (2006.01)
(Continued)

(52) U.S. Cl.
CPC .......... *A61B 18/1492* (2013.01); *A61B 19/5244* (2013.01); *A61B 2017/003* (2013.01);
(Continued)

(58) Field of Classification Search
CPC ................................ A61B 18/24; A61B 18/22
USPC .................................... 606/15, 16; 607/88, 89
See application file for complete search history.

(56) References Cited

U.S. PATENT DOCUMENTS

| 1,791,794 A | 2/1931 | Chesney |
| 4,469,098 A | 9/1984 | Davi |

(Continued)

FOREIGN PATENT DOCUMENTS

| EP | 0 195 375 A2 | 9/1986 |
| EP | 0 441 040 A2 | 8/1991 |

(Continued)

OTHER PUBLICATIONS

U.S. Appl. No. 11/281,853, filed Nov. 17, 2005, Sharareh et al.
(Continued)

*Primary Examiner* — William Thomson
*Assistant Examiner* — Jeffrey Lipitz
(74) *Attorney, Agent, or Firm* — Christie, Parker & Hale, LLP

(57) ABSTRACT

A catheter is adapted to ablate tissue and provide lesion qualitative information on a real time basis, having an ablation tip section with a generally omni-directional light diffusion chamber with one openings to allow light energy in the chamber to radiate the tissue and return to the chamber. The chamber is irrigated at a positive pressure differential to continuously flush the opening with fluid. The light energy returning to the chamber from the tissue conveys a tissue parameter, including without limitation, lesion formation, depth of penetration of lesion, cross-sectional area of lesion, formation of char during ablation, recognition of char during ablation, recognition of char from non-charred tissue, formation of coagulum around the ablation site, differentiation of coagulated from non-coagulated blood, differentiation of ablated from healthy tissue, tissue proximity, and recognition of steam formation in the tissue for prevention of steam pop.

33 Claims, 13 Drawing Sheets

(51) Int. Cl.
*A61B 17/00* (2006.01)
*A61B 18/00* (2006.01)

(52) U.S. Cl.
CPC ............ *A61B2017/00057* (2013.01); *A61B 2017/00084* (2013.01); *A61B 2018/00589* (2013.01); *A61B 2018/00791* (2013.01); *A61B 2019/547* (2013.01); *A61B 2218/002* (2013.01)

(56) References Cited

U.S. PATENT DOCUMENTS

| | | | |
|---|---|---|---|
| 4,587,972 A | 5/1986 | Morantte, Jr. |
| 4,669,098 A | 5/1987 | Boatwright |
| 4,669,467 A | 6/1987 | Willett et al. |
| 4,672,961 A | 6/1987 | Davies |
| 4,736,743 A | 4/1988 | Daikuzono |
| 4,819,632 A | 4/1989 | Davies |
| 4,860,743 A | 8/1989 | Abela |
| 5,041,109 A | 8/1991 | Abela |
| 5,061,265 A | 10/1991 | Abela et al. |
| 5,147,348 A | 9/1992 | Leckrone et al. |
| 5,151,096 A | 9/1992 | Khoury |
| 5,248,311 A | 9/1993 | Black et al. |
| 5,267,996 A | 12/1993 | Fletcher |
| 5,370,608 A | 12/1994 | Sahota et al. |
| 5,370,640 A | 12/1994 | Kolff |
| 5,391,199 A | 2/1995 | Ben-Haim |
| 5,443,489 A | 8/1995 | Ben-Haim |
| 5,480,422 A | 1/1996 | Ben-Haim |
| 5,546,951 A | 8/1996 | Ben-Haim |
| 5,558,091 A | 9/1996 | Acker et al. |
| 5,568,809 A | 10/1996 | Ben-Haim |
| 5,630,809 A | 5/1997 | Connor |
| 5,643,253 A | 7/1997 | Baxter et al. |
| 5,688,264 A | 11/1997 | Ren et al. |
| 5,693,043 A | 12/1997 | Kittrell et al. |
| 5,807,248 A | 9/1998 | Mills |
| 5,807,389 A | 9/1998 | Gardetto et al. |
| 5,830,209 A | 11/1998 | Savage et al. |
| 5,861,020 A | 1/1999 | Schwarzmaier |
| 5,964,757 A | 10/1999 | Ponzi |
| 5,997,571 A | 12/1999 | Farr et al. |
| 6,016,452 A | 1/2000 | Kasevich |
| 6,053,912 A | 4/2000 | Panescu et al. |
| 6,071,302 A | 6/2000 | Sinofsky et al. |
| 6,106,516 A | 8/2000 | Massengill |
| 6,120,476 A | 9/2000 | Fung et al. |
| 6,143,018 A | 11/2000 | Beuthan et al. |
| 6,168,594 B1 | 1/2001 | LaFontaine et al. |
| 6,171,275 B1 | 1/2001 | Webster, Jr. |
| 6,171,303 B1 | 1/2001 | Ben-Haim et al. |
| 6,241,666 B1 | 6/2001 | Pomeranz et al. |
| 6,423,055 B1 | 7/2002 | Farr et al. |
| 6,464,694 B1 | 10/2002 | Massengill |
| 6,468,260 B1 | 10/2002 | Bumbalough et al. |
| 6,579,285 B2 | 6/2003 | Sinofsky |
| 6,602,242 B1 | 8/2003 | Fung et al. |
| 6,692,486 B2 | 2/2004 | Jaafar et al. |
| 6,736,808 B1 | 5/2004 | Motamedi et al. |
| 6,923,805 B1 | 8/2005 | LaFontaine et al. |
| 6,953,457 B2 | 10/2005 | Farr et al. |
| 2001/0012429 A1 | 8/2001 | Wach et al. |
| 2002/0022834 A1 | 2/2002 | Simpson et al. |
| 2002/0026188 A1 | 2/2002 | Balbierz et al. |
| 2002/0045848 A1 | 4/2002 | Jaafar et al. |
| 2002/0183729 A1 | 12/2002 | Farr et al. |
| 2003/0004506 A1 | 1/2003 | Messing |
| 2003/0040657 A1 | 2/2003 | Yamaya et al. |
| 2004/0015061 A1 | 1/2004 | Currier et al. |
| 2004/0015138 A1 | 1/2004 | Currier et al. |
| 2004/0158302 A1 | 8/2004 | Chornenky et al. |
| 2005/0059962 A1 | 3/2005 | Phan et al. |
| 2005/0065504 A1 | 3/2005 | Melsky et al. |
| 2005/0070894 A1 | 3/2005 | McClurken |
| 2005/0096643 A1 | 5/2005 | Brucker et al. |
| 2005/0143721 A1 | 6/2005 | Brucker et al. |
| 2005/0143722 A1 | 6/2005 | Brucker et al. |
| 2005/0159734 A1 | 7/2005 | Brucker et al. |
| 2005/0165462 A1 | 7/2005 | Bays et al. |
| 2005/0171520 A1 | 8/2005 | Farr et al. |
| 2005/0222557 A1 | 10/2005 | Baxter et al. |
| 2005/0267452 A1 | 12/2005 | Farr et al. |
| 2006/0122587 A1 | 6/2006 | Sharareh |
| 2006/0184165 A1 | 8/2006 | Webster, Jr. et al. |
| 2007/0287998 A1 | 12/2007 | Sharareh et al. |
| 2008/0097220 A1 | 4/2008 | Lieber et al. |
| 2008/0119694 A1 | 5/2008 | Lee |
| 2008/0154257 A1 | 6/2008 | Sharareh et al. |
| 2009/0005773 A1 | 1/2009 | Beeckler et al. |

FOREIGN PATENT DOCUMENTS

| | | |
|---|---|---|
| WO | WO 95/02995 | 2/1995 |
| WO | WO 2007/127228 A2 | 11/2007 |
| WO | WO 2007/146995 A1 | 12/2007 |

OTHER PUBLICATIONS

Extended European Search Report dated Jun. 16, 2010 for EP Patent Application No. 10075155.1 (3 pages).
European Patent Office, Partial European Search Report of EP 08253725.9, dated Apr. 22, 2009, 4 pgs.
International Search Report and Written Opinion for International Application No. PCT/US2007/071107, mailed Nov. 19, 2007.

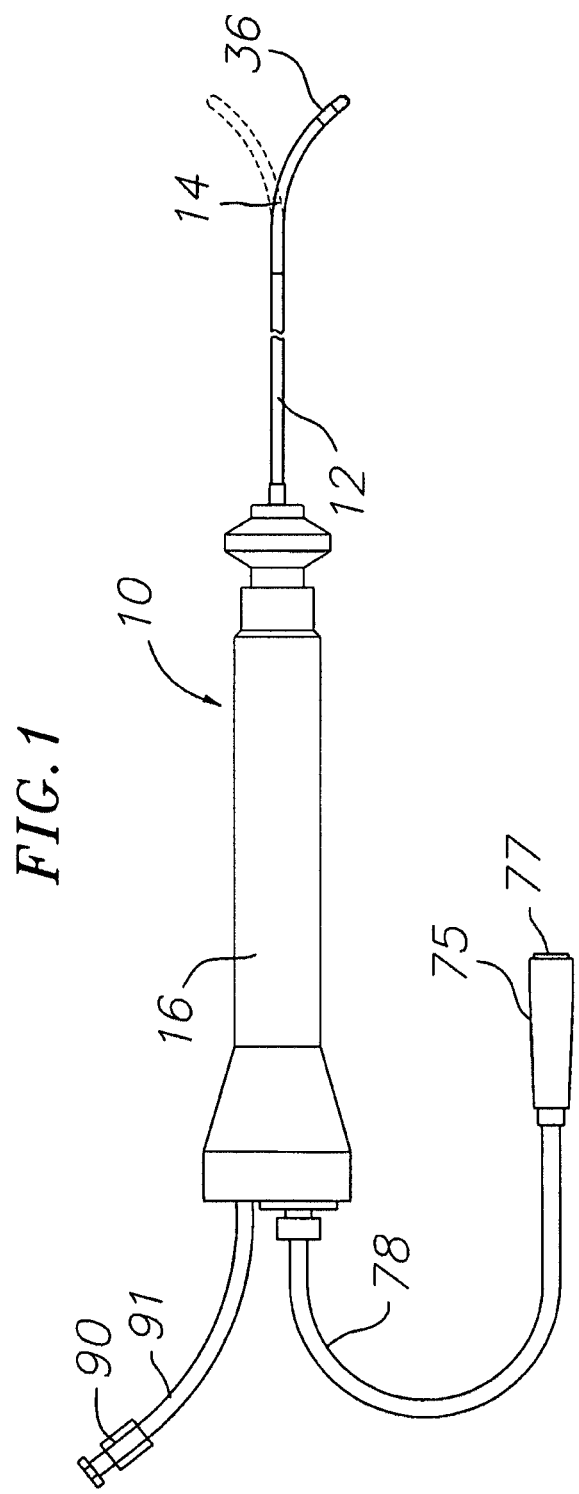

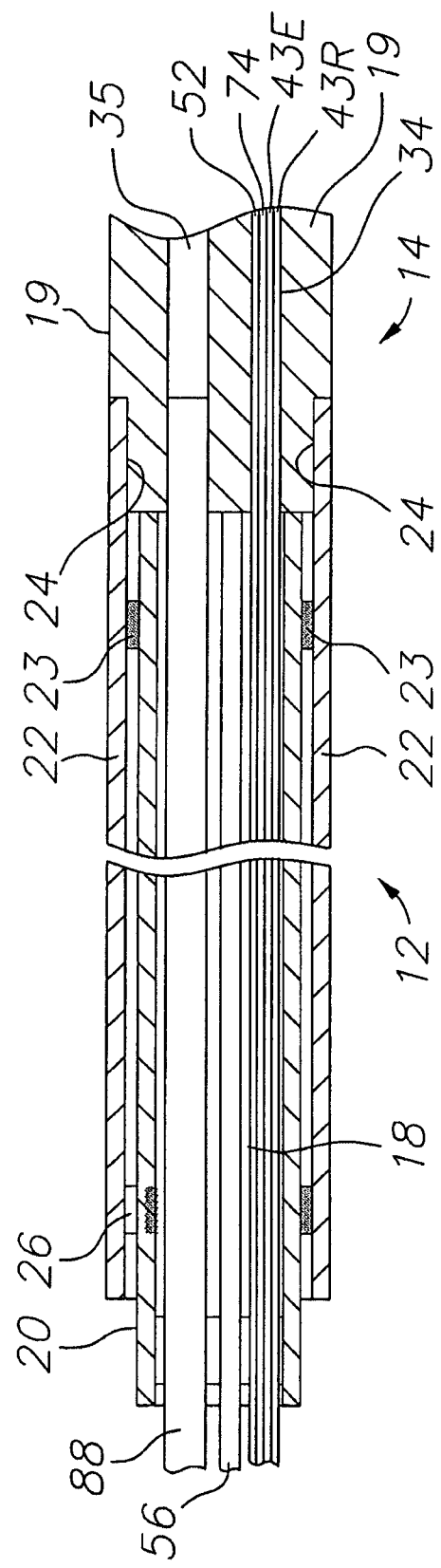

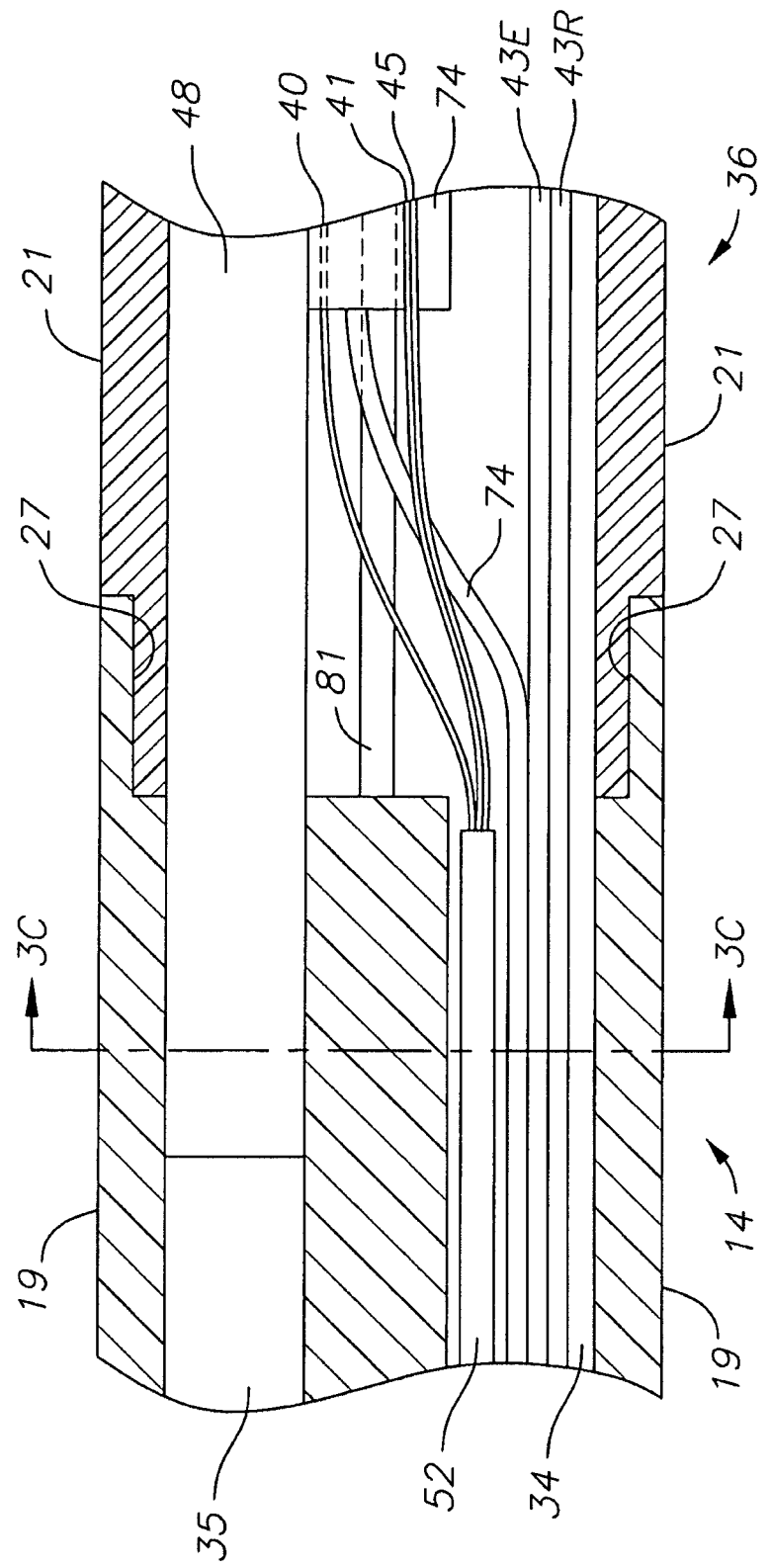

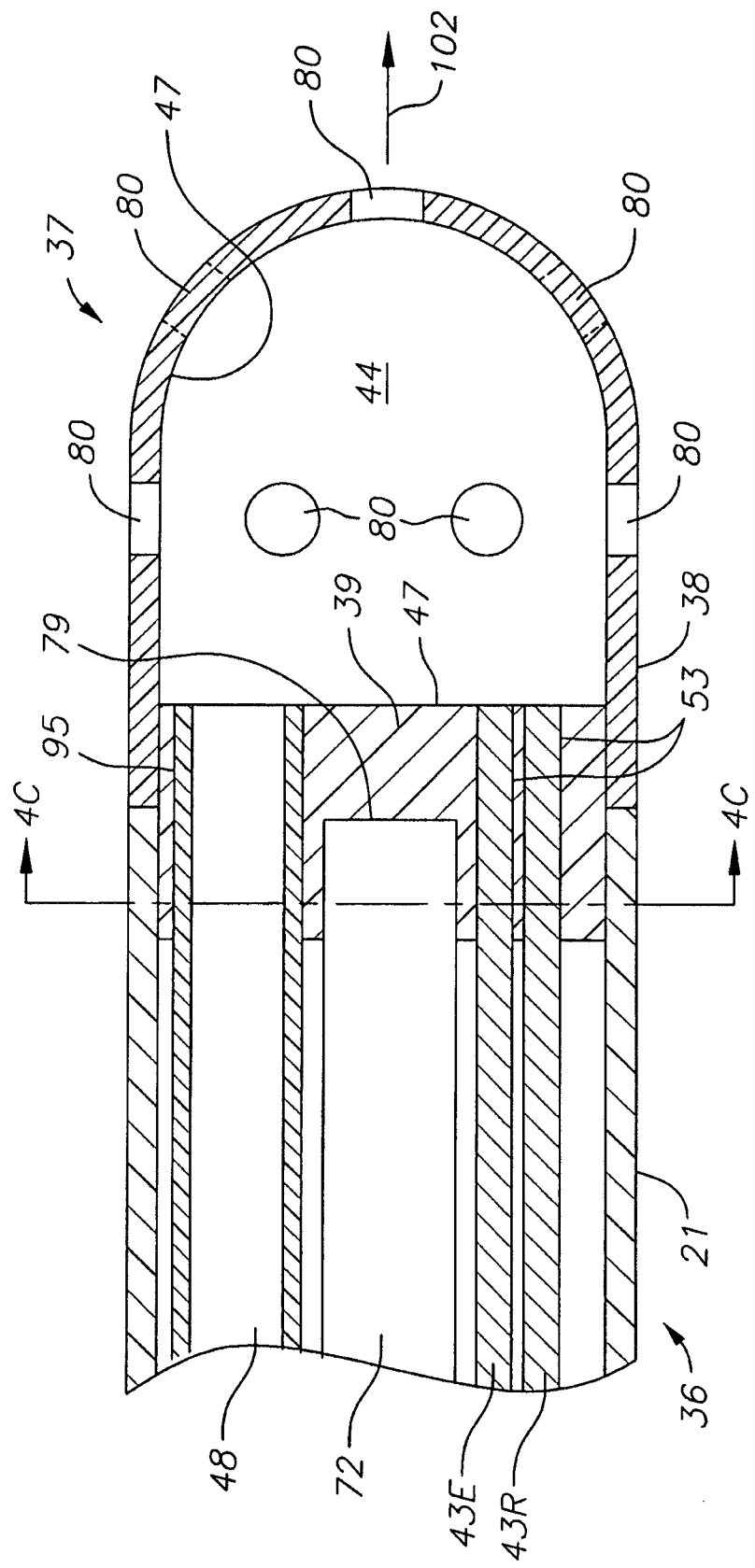

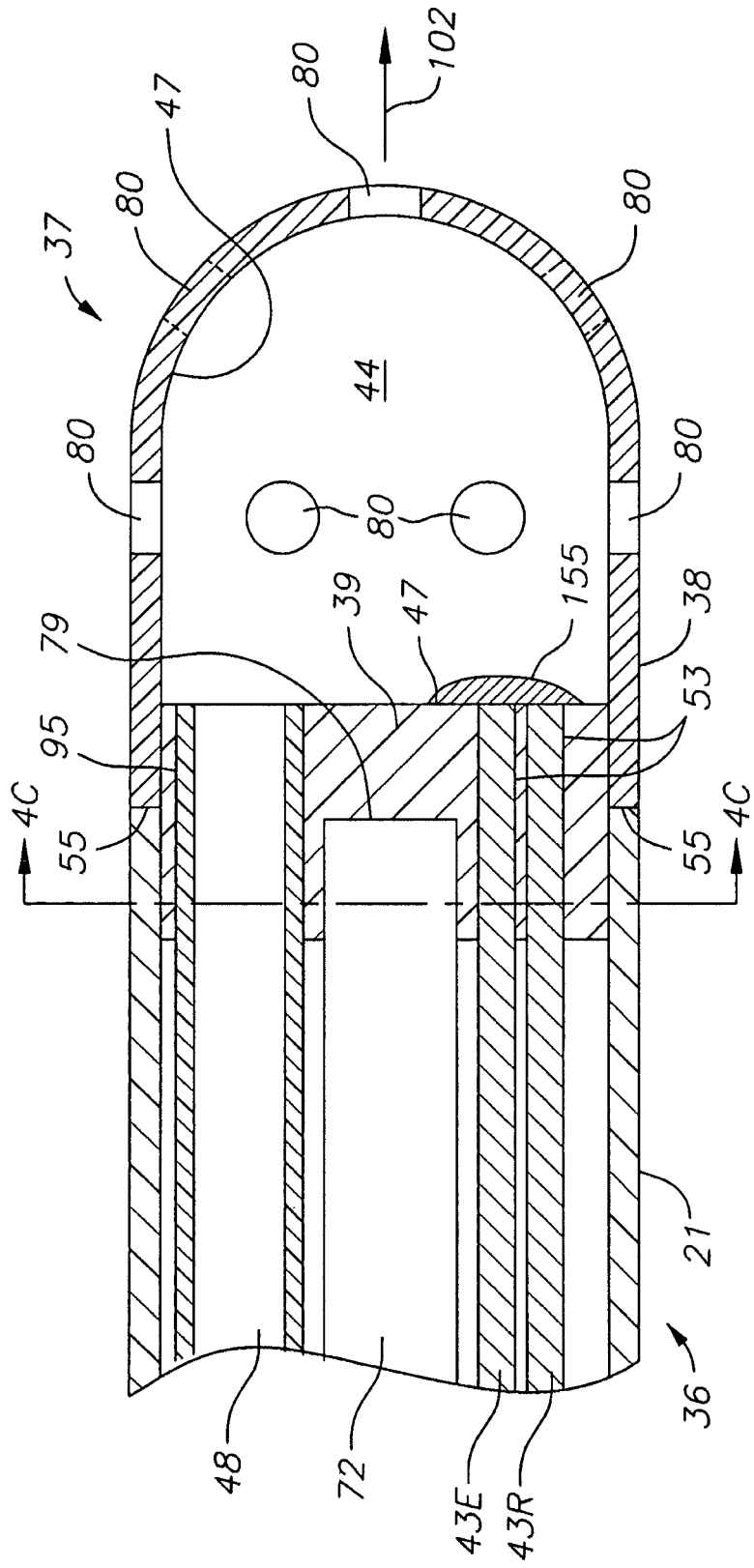

CATHETER WITH OMNI-DIRECTIONAL OPTICAL LESION EVALUATION

This application is continuation of and claims priority to and the benefit of U.S. application Ser. No. 11/417,092 filed May 2, 2006, the entire content of which is incorporated herein.

FIELD OF INVENTION

1. Field of Invention

The present invention relates to ablation catheters, and in particular to ablation catheters with lesion monitoring.

2. Background

For certain types of minimally invasive medical procedures, real time information regarding the condition of the treatment site within the body is unavailable. This lack of information inhibits the clinician when employing catheter to perform a procedure. An example of such procedures is tumor and disease treatment in the liver and prostate. Yet another example of such a procedure is surgical ablation used to treat atrial fibrillation. This condition in the heart causes abnormal electrical signals, known as cardiac arrhythmias, to be generated in the endocardial tissue resulting in irregular beating of the heart.

The most frequent cause of cardiac arrhythmias is an abnormal routing of electricity through the cardiac tissue. In general, most arrhythmias are treated by ablating suspected centers of this electrical misfiring, thereby causing these centers to become inactive. Successful treatment, then, depends on the location of the ablation within the heart as well as the lesion itself. For example, when treating atrial fibrillation, an ablation catheter is maneuvered into the right or left atrium where it is used to create ablation lesions in the heart. These lesions are intended to stop the irregular beating of the heart by creating non-conductive barriers between regions of the atria that halt passage through the heart of the abnormal electrical activity.

The lesion should be created such that electrical conductivity is halted in the localized region (transmurality), but care should be taken to prevent ablating adjacent tissues. Furthermore, the ablation process can also cause undesirable charring of the tissue and localized coagulation, and can evaporate water in the blood and tissue leading to steam pops.

Currently, lesions are evaluated following the ablation procedure, by positioning a mapping catheter in the heart where it is used to measure the electrical activity within the atria. This permits the physician to evaluate the newly formed lesions and determine whether they will function to halt conductivity. It if is determined that the lesions were not adequately formed, then additional lesions can be created to further form a line of block against passage of abnormal currents. Clearly, post ablation evaluation is undesirable since correction requires additional medical procedures. Thus, it would be more desirable to evaluate the lesion as it is being formed in the tissue.

A known method for evaluating lesions as they are formed is to measure electrical impedance. Biochemical differences between ablated and normal tissue can result in changes in electrical impedance between the tissue types. Although impedance is routinely monitored during electrophysiologic therapy, it is not directly related to lesion formation. Measuring impedance merely provides data as to the location of the tissue lesion but does not give qualitative data to evaluate the effectiveness of the lesion.

Another approach is to measure the electrical conductance between two points of tissue. This process, known as lesion pacing, can also determine the effectiveness of lesion therapy. This technique, however, measures only the success or lack thereof from each lesion, and yields no real-time information about the lesion formation.

Thus, there is a need for a catheter capable of measuring lesion formation in real-time, as well as detecting the formation of charred tissue and coagulated blood around the ablation catheter. Because a catheter may assume various orientation angles at the ablation site, there is a further need for a catheter that is capable of such measuring and detecting whether the catheter is parallel, perpendicular or at an angle to the tissue. Moreover, where such measuring and detecting are accomplished through optical spectroscopy, there is a also a need for a catheter that can minimize obstruction of optical pathways between the catheter and the tissue undergoing ablation.

SUMMARY OF THE INVENTION

The present invention is directed to a catheter that is adapted for ablation and provides optically-based lesion quantitative information on a real time basis. The catheter includes a catheter body and a tip section configured for ablating tissue. In accordance with the invention, the tip section has a light diffusion chamber with openings through which light energy in the chamber can radiate and return from the tissue at a plurality of angles relative to the catheter. Additionally, the chamber may be irrigated with fluid, for example, saline, at a positive pressure differential to continuously flush the openings with fluid. The light energy returning to the chamber from the tissue conveys tissue parameters that can be evaluated using optical spectroscopy. These parameters include, without limitation, lesion formation, depth of penetration of lesion, and cross-sectional area of lesion, formation of char during ablation, recognition of char during ablation, recognition of char from non-charred tissue, formation of coagulum around the ablation site, differentiation of coagulated from non-coagulated blood, differentiation of ablated from healthy tissue, tissue proximity, evaluation of tissue health, status, and disease state, and recognition of steam formation in the tissue for prevention of steam pop.

In one embodiment of the catheter, light energy for radiating tissue is delivered to the light diffusion chamber of tip section by a first optical waveguide, for example, a fiber optic cable. Most if not all of the light energy is specularly or diffusely scattered in the chamber before exiting through the openings to radiate the tissue. Upon reflection by the tissue back into the chamber through the openings, most if not all of the light energy is again scattered by the chamber before it is collected by a second optical guide, for example, another fiber optic cable, for optical processing and evaluation by a detection component and a quantification apparatus. In an alternative embodiment, a single optical waveguide may be used for delivering the radiation light energy to the chamber and collecting the light energy from the chamber for optical processing and evaluation system.

Advantageously, the catheter is functional for ablation and lesion evaluation for nearly all angles of orientation with the tissue. To that end, the light diffusion chamber is defined by portions of the tip electrode that are oriented at different angles relative to the longitudinal axis of the tip electrode. In one embodiment, there are a first portion that is generally perpendicular to the longitudinal axis, a second portion that is angled between about zero and 90 degrees to the longitudinal axis, preferably between about 20 to 70 degrees, and more preferably about 45 degrees, and a third portion that is generally parallel to the longitudinal axis. At least one opening is configured in each portion of the tip electrode so that light energy in the reflection chamber can radiate the tissue and re-enter the reflection chamber for nearly all angles of orientation relative to the catheter tip section. Accordingly, these portions of the tip electrode and the openings provided therein render the reflection chamber a generally omni-directional radiator and collector of light energy for ablation tissue optical spectroscopy.

With adaptations for light energy to exit and enter the chamber for nearly all angles of orientation, the catheter can ablate and facilitate lesion evaluation in real time whether the catheter is lying on the tissue, standing on its distal end or at an angle with the tissue. In a detailed embodiment, there are a plurality of openings in the second and third portions. In a more detailed embodiment, there are one opening in the first portion, three openings in the second portion and six openings in the third portion.

The catheter may be uni or bidirectionally with a deflectable intermediate section between the catheter body and the tip section. The tip section may include a tip electrode having a shell and a plug whose assembly defines the chamber within the tip electrode, wherein the tip electrode is constructed of a thermally and electrically conductive material. The catheter may carry a temperature sensor and/or an electromagnetic location sensor carried at or near the tip section for producing electrical signals indicative of a location of the electromagnetic location sensor.

The present catheter and optical system are designed to use light in conjunction with irrigation and the technology of RF ablation. Advantageously, the light used to monitor and assess the lesion is generally not affected by the portion of the electromagnetic radiation used for ablation. Moreover, the bandwidth used for monitoring and assessing also transmits through blood with minimal attenuations. The fiber optics are used and disposed in the catheter in a manner that avoids contact with tissue, which can increase the operative lifetime of the catheter and minimize damages caused by abrasion to the fiber optics. Furthermore, the fiber optics are disposed in a tip section with minimal bent or strain but increased angular coverage, which can minimize fiber optics breakage during assembly and use, as well as reduce nonlinear optical effects caused by orientation of the fiber optics. In addition, the use of fiber optics to emit and receive light is a generally temperature neutral process that adds little if any measurable heat to surrounding blood or tissue.

BRIEF DESCRIPTION OF THE DRAWINGS

These and other features and advantages of the present invention will be better understood by reference to the following detailed description when considered in conjunction with the accompanying drawings wherein:

FIG. 1 is a side cross-sectional view of an embodiment of the catheter of the invention.

FIG. 2B is a side cross-sectional view of an embodiment of a catheter body according to the invention, including the junction between the catheter body and intermediate section taken along a second diameter generally perpendicular to the first diameter of FIG. 2A.

FIG. 3A is a side cross-sectional view of an embodiment of a catheter body according to the invention, including the junction between the intermediate section and tip section taken along a first diameter.

FIG. 4A is a side cross-sectional view of a catheter tip section showing an embodiment having an irrigated omni-directional light diffusion chamber taken along a first diameter.

FIG. 10. is a side view of an alternative embodiment of a tip section.

DETAILED DESCRIPTION OF THE INVENTION

Figure 2A:
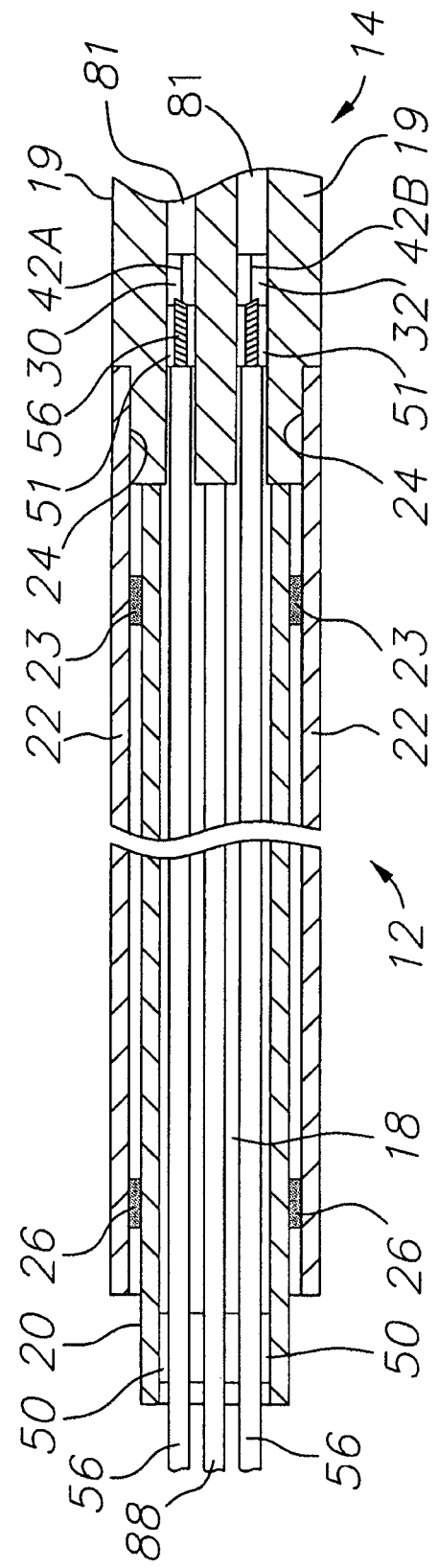
FIG. 2A is a side cross-sectional view of an embodiment of a catheter body according to the invention, including the junction between the catheter body and intermediate section taken along a first diameter.

As shown in FIGS. 1-7, catheter 10 comprises an elongated catheter body 12 having proximal and distal ends, a potentially deflectable (uni- or bi-directionally) intermediate section 14 at the distal end of the catheter body 12, a tip section 36 at the distal end of the intermediate section, and a control handle 16 at the proximal end of the catheter body 12.

With reference to FIGS. 1, 2A and 2B, the catheter body 12 comprises an elongated tubular construction having a single, axial or central lumen 18. The catheter body 12 is flexible, i.e., bendable, but substantially non-compressible along its length. The catheter body 12 can be of any suitable construction and made of any suitable material. A construction comprises an outer wall 22 made of an extruded plastic. The outer wall 22 may comprise an imbedded braided mesh of stainless steel or the like to increase torsional stiffness of the catheter body 12 so that, when the control handle 16 is rotated, the catheter body 12, the intermediate section 14 and the tip section 36 of the catheter 10 will rotate in a corresponding manner.

Extending through the single lumen 18 of the catheter body 12 are components, for example, lead wire and thermocouple wires protected by a sheath, fiber optic cables, a first irrigation tube segment, compression coils through which puller wires extend, and an electromagnetic sensor cable. A single lumen catheter body can be preferred over a multi-lumen body because it has been found that the single lumen body permits better tip control when rotating the catheter. The single lumen permits the various components such as the lead wires, infusion tube, and the puller wire surrounded by the compression coil to float freely within the catheter body. If such wires, tube and cables were restricted within multiple lumens, they tend to build up energy when the handle is rotated, resulting in the catheter body having a tendency to rotate back if, for example, the handle is released, or if bent around a curve, to flip over, either of which are undesirable performance characteristics.

The outer diameter of the catheter body 12 is not critical, but is preferably no more than about 8 french, more preferably 7 french. Likewise the thickness of the outer wall 22 is not critical, but is thin enough so that the central lumen 18 can accommodate the aforementioned components. The inner surface of the outer wall 22 may be lined with a stiffening tube 20, which can be made of any suitable material, such as polyimide or nylon. The stiffening tube 20, along with the braided outer wall 22, provides improved torsional stability while at the same time minimizing the wall thickness of the catheter, thus maximizing the diameter of the central lumen 18. The outer diameter of the stiffening tube 20 is about the same as or slightly smaller than the inner diameter of the outer wall 22. Polyimide tubing may be preferred for the stiffening tube 20 because it may be very thin walled while still providing very good stiffness. This maximizes the diameter of the central lumen 18 without sacrificing strength and stiffness.

Figure 3B:
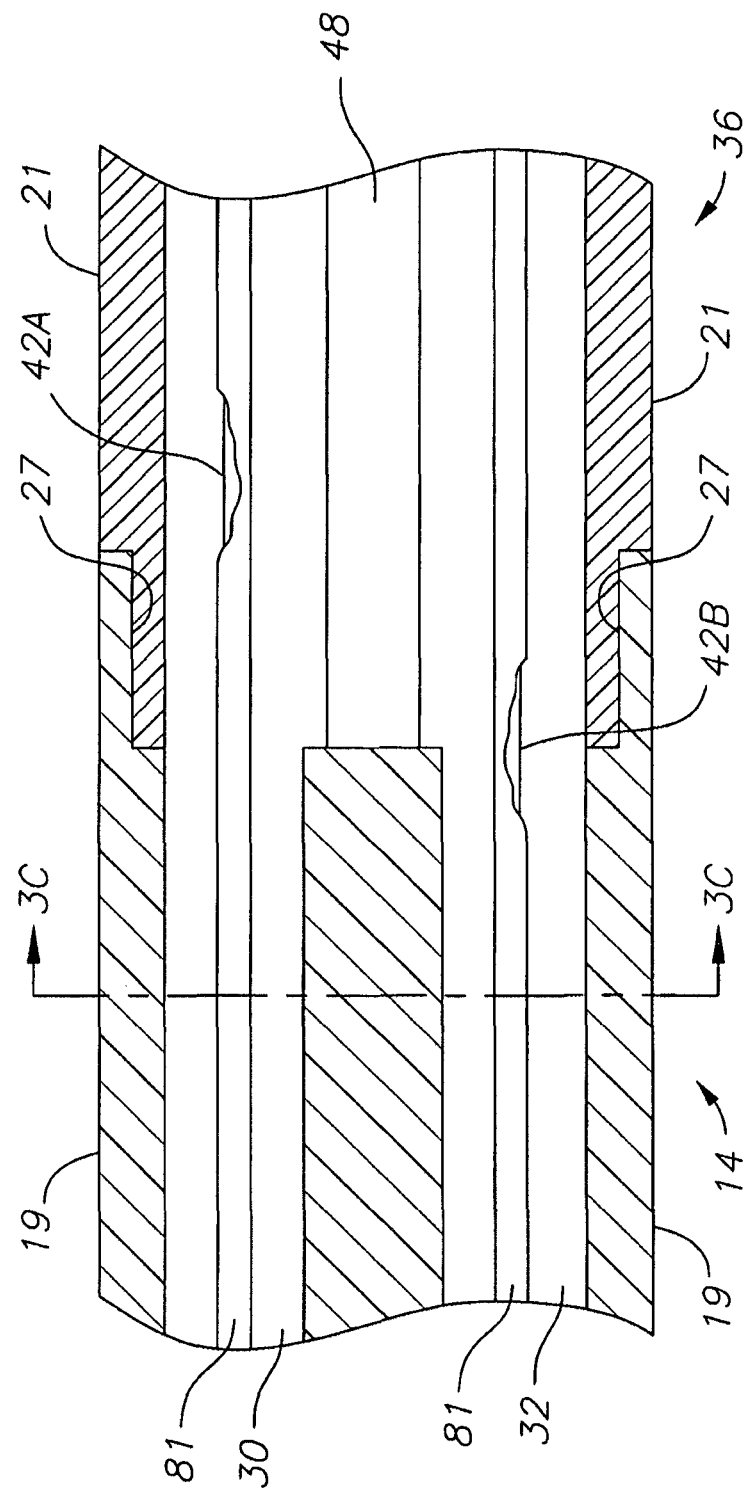
FIG. 3B is a side cross-sectional view of an embodiment of a catheter body according to the invention, including the junction between the intermediate section and tip section taken along a second diameter generally perpendicular to the first diameter of FIG. 3A.
Figure 3C:
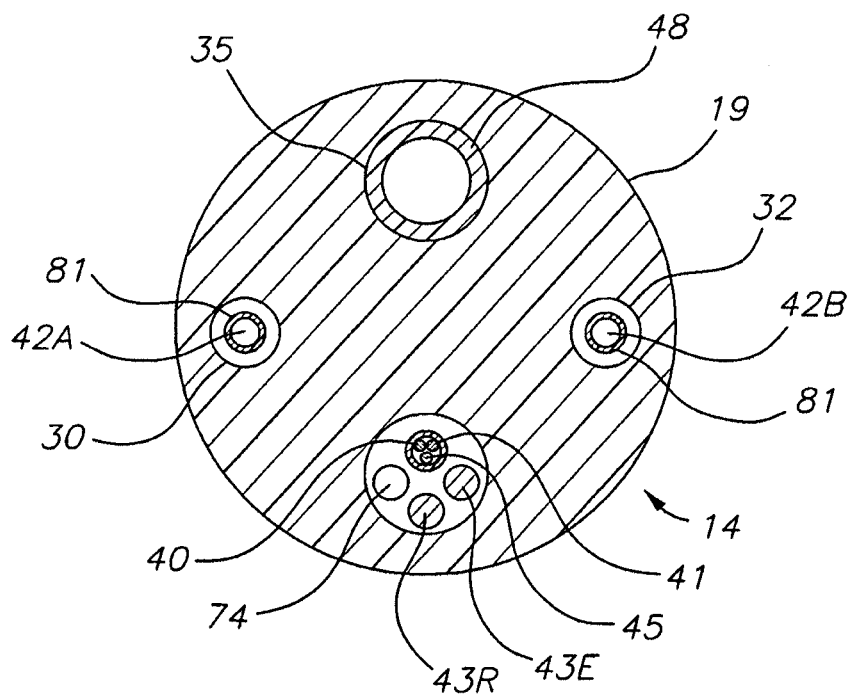
FIG. 3C is a longitudinal cross-sectional view of an embodiment of an intermediate section of FIGS. 3A and 3B, taken along line 3C-3C.

Referring also to FIGS. 3A, 3B and 3C, the intermediate section 14 comprises a shorter section of tubing 19 having multiple lumens. The tubing 19 is made of a suitable non-toxic material that is preferably more flexible than the catheter body 12. A suitable material for the tubing 19 is non-braided polyurethane. The outer diameter of the intermediate section 14, like that of the catheter body 12, is preferably no greater than about 8 french, more preferably 7 french. The size and number of the lumens is not critical. In an embodiment, the intermediate section 14 has an outer diameter of about 7 french (0.092 inch). The tubing has a first off-axis lumen 30 and a second off-axis lumen 32 that are generally about the same size, each having a diameter of from about 0.020 inch to about 0.024 inch, preferably 0.022 inch, along with a third off-axis lumen 34 and a fourth off-axis lumen 35, each having a slightly larger diameter of from about 0.032 inch to about 0.038 inch, preferably 0.036 inch.

Referring to FIGS. 2A and 2B, a means for attaching the catheter body 12 to the intermediate section 14 comprises an outer circumferential notch 24 configured in the proximal end of the tubing 19 that receives the inner surface of the outer wall 22 of the catheter body 12. The intermediate section 14 and catheter body 12 are attached by glue or the like. Before the intermediate section 14 and catheter body 12 are attached, the stiffening tube 20 is inserted into the catheter body 12. The distal end of the stiffening tube 20 is fixedly attached near the distal end of the catheter body 12 by forming a glue joint 23 with polyurethane glue or the like. Preferably a small distance, e.g., about 3 mm, is provided between the distal end of the catheter body 12 and the distal end of the stiffening tube 20 to permit room for the catheter body 12 to receive the notch 24 of the intermediate section 14. If no compression coil is used, a force is applied to the proximal end of the stiffening tube 20, and, while the stiffening tube 20 is under compression, a first glue joint (not shown) is made between the stiffening tube 20 and the outer wall 22 by a fast drying glue, e.g. cyanoacrylate. Thereafter a second glue joint 26 is formed between the proximal ends of the stiffening tube 20 and outer wall 22 using a slower drying but stronger glue, e.g., polyurethane.

If desired, a spacer can be located within the catheter body between the distal end of the stiffening tube and the proximal end of the tip section. The spacer provides a transition in flexibility at the junction of the catheter body and intermediate section, which allows this junction to bend smoothly without folding or kinking. A catheter having such a spacer is described in U.S. patent application Ser. No. 08/924,616, entitled "Steerable Direct Myocardial Revascularization Catheter", the entire disclosure of which is incorporated herein by reference.

Figure 4B:
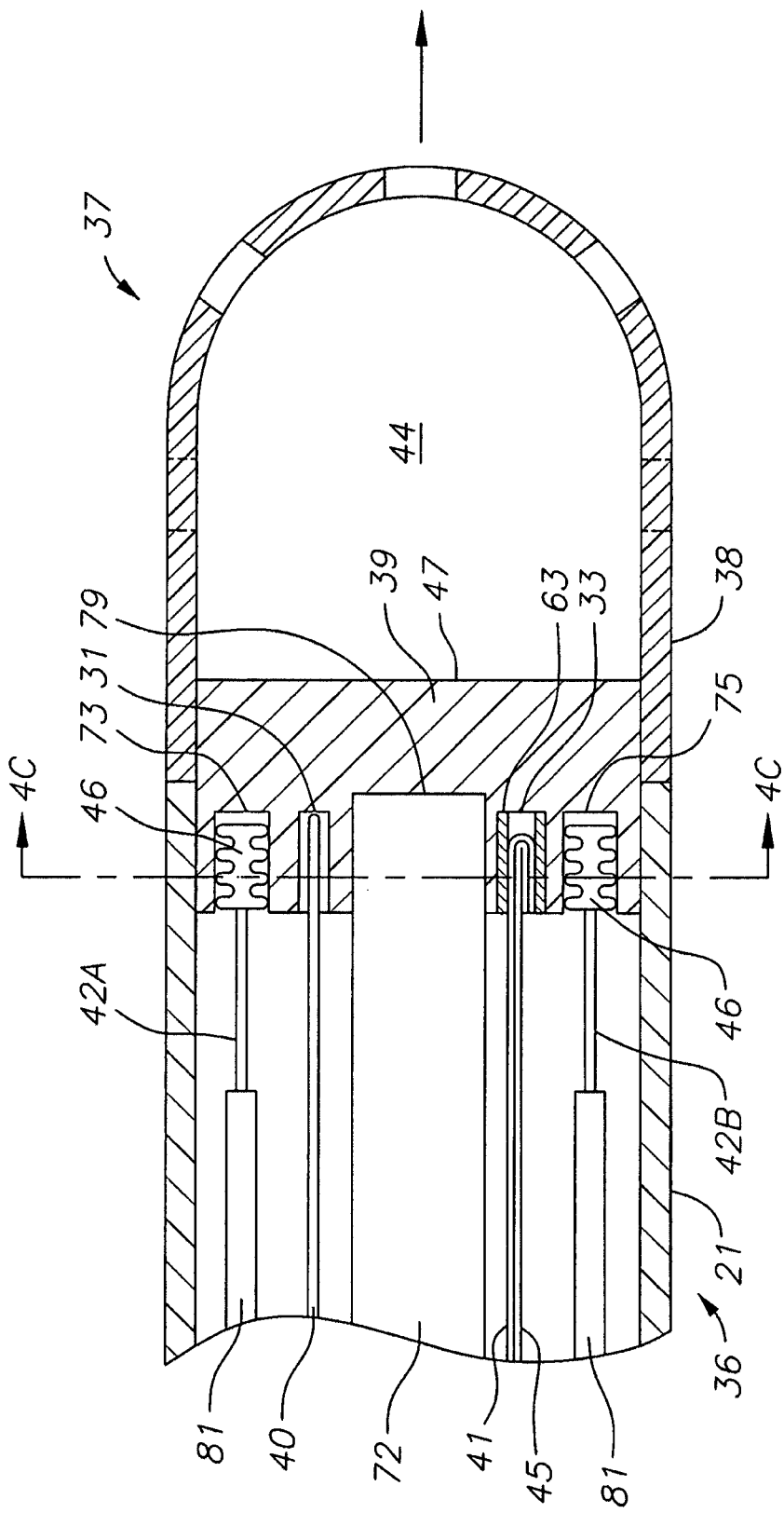
FIG. 4B is a side cross-sectional view of an embodiment of a catheter tip section taken along a second diameter
Figure 4C:
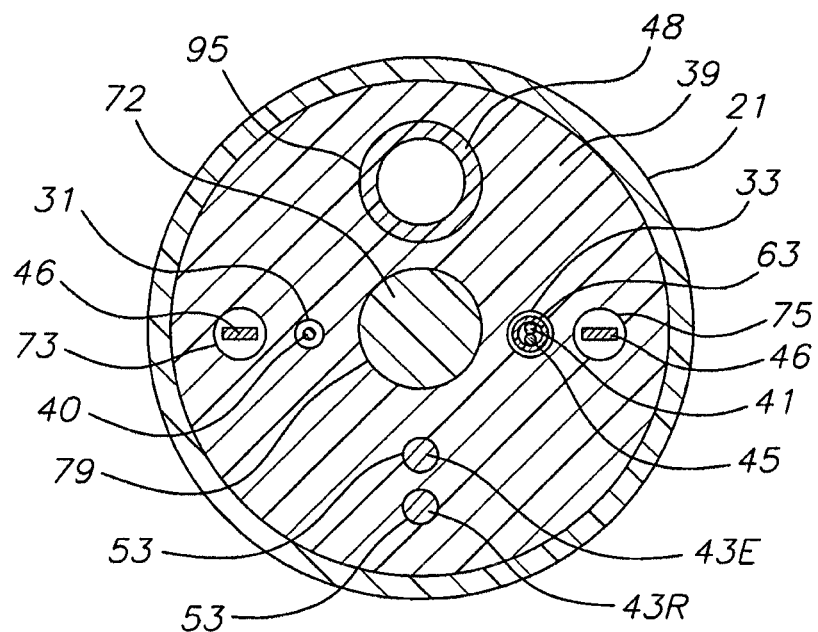
FIG. 4C is a longitudinal cross-sectional view of an embodiment of a catheter tip section of FIGS. 4A and 4B, taken along line 4C-4C.

As illustrated in FIGS. 4A-4C, extending from the distal end of the intermediate section 14 is the tip section 36 that includes a tip electrode 37 and a plastic housing 21 extending between the tubing 19 and the tip electrode 37. Preferably the tip electrode 37 has a diameter about the same as the outer diameter of the tubing 19 of the intermediate section 14. The plastic housing 21 is preferably made of polyetheretherketone (PEEK) and may be about 1 cm long. Its proximal end comprises an outer circumferential notch 27 (FIGS. 3A and 3B) that receives the inner surface of the tubing 19 of the intermediate section 14. The intermediate section 14 and the plastic housing 21 are attached by glue or the like.

As shown in the embodiment of FIGS. 4A and 4B, the tip electrode 37 has a generally hollow distal portion and is of a two-piece construction. In particular, the tip electrode comprises a shell 38 of generally uniform thickness and a press-fit plug 39 positioned at or near the proximal end of the shell. The shell and the plug are formed from any suitable material that is both thermally and electrically conductive which allows for radio frequency ablation using an RF generator. Such suitable materials include, without limitation, platinum, gold alloy, or palladium alloy. A suitable tip electrode and method for manufacturing same are disclosed in U.S. application Ser. No. 11/058,434, filed Feb. 14, 2005, the entire disclosure of which is hereby incorporated by reference.

A tip electrode may have an effective length, i.e., from its distal end to the distal end of the housing 21, between about 3.5 mm to about 7.5 mm, and an actual length, i.e., from its distal end to its proximal end, between about 4.0 mm to about 8 .mm. As shown in FIGS. 4A and 4B, the tip electrode 37 is attached to the plastic housing 21 with glue at edge 55 which is located at about a midpoint between the distal and proximal ends of the plug 39. The wires, cables and tube that extend into the plug 39 help to keep the tip electrode in place on the tip section 36.

The tip electrode 37 is energized for RF ablation by a lead wire 40 that extends through the third lumen 34 of intermediate section 14, the central lumen 18 of the catheter body 12, and the control handle 16, and terminates at its proximal end in an input jack (not shown) that may be plugged into an appropriate monitor (not shown). The portion of the lead wire 40 extending through the central lumen 18 of the catheter body 12, control handle 16 and distal end of the intermediate section 14 is enclosed within a protective sheath 52, which can be made of any suitable material, preferably Teflon®. The protective sheath 52 is anchored at its distal end to the distal end of the intermediate section 14 by gluing it in the lumen 34 with polyurethane glue or the like. The lead wire 40 is attached to the tip electrode 37 by any conventional technique. In the illustrated embodiment, connection of the lead wire 40 to the tip electrode 37 is accomplished, for example, by welding the distal end of the lead wire 40 into a first blind hole 31 (FIG. 4B) in the plug 39 of the tip electrode 37.

A temperature sensing means is provided for the tip electrode 37 in the disclosed embodiment. Any conventional temperature sensing means, e.g., a thermocouple or thermistor, may be used. With reference to FIG. 4B, a suitable temperature sensing means for the tip electrode 37 comprises a thermocouple formed by a wire pair. One wire of the wire pair is a copper wire 41, e.g., a number 40 copper wire. The other wire of the wire pair is a constantan wire 45, which gives support and strength to the wire pair. The wires 41 and 45 of the wire pair are electrically isolated from each other except at their distal ends where they contact and are twisted together, covered with a short piece of plastic tubing 63, e.g., polyimide, and covered with epoxy. The plastic tubing 63 is then attached in a second blind hole 33 of the tip electrode 37, by epoxy or the like. The wires 41 and 45 extend through the third lumen 34 in the intermediate section 14. Within the catheter body 12 the wires 41 and 45 extend through the central lumen 18 within the protective sheath 52 along with the lead wires 40. The wires 41 and 45 then extend out through the control handle 16 and to a connector (not shown) connectable to a temperature monitor (not shown). Alternatively, the temperature sensing means may be a thermistor. A suitable thermistor for use in the present invention is Model No. AB6N2-GC14KA143T/37C sold by Thermometrics (New Jersey).

Referring to FIGS. 2A, 3B and 4B, a pair of puller wires 42A and 42B extend through the catheter body 12, are anchored at their proximal ends to the control handle 16, and are anchored at their distal ends to the tip section 36. The puller wires are made of any suitable metal, such as stainless steel or Nitinol, and is preferably coated with Teflon®. or the like. The coating imparts lubricity to the puller wires. Each puller wire preferably has a diameter ranging from about 0.006 to about 0.010 inches.

A compression coil 56 is situated within the catheter body 12 in surrounding relation to each puller wire. The compression coils 56 extend from the proximal end of the catheter body 12 to the proximal end of the intermediate section 14 (FIG. 2A). The compression coils are made of any suitable metal, preferably stainless steel. Each compression coil is tightly wound on itself to provide flexibility, i.e., bending, but to resist compression. The inner diameter of the compression coil is preferably slightly larger than the diameter of the puller wires 42. The Teflon®. coating on the puller wires allows them to slide freely within the compression coils. If desired, particularly if the lead wire 40 is not enclosed by a protective sheath 52, the outer surface of the compression coils can be covered by a flexible, non-conductive sheath, e.g., made of polyimide tubing, to prevent contact between the compression coils and any other wires within the catheter body 12.

As shown in FIG. 2A, each compression coil 56 is anchored at its proximal end to the proximal end of the stiffening tube 20 in the catheter body 12 by glue joint 50 and at its distal end to the intermediate section 14 by glue joint 51. Both glue joints 50 and 51 preferably comprise polyurethane glue or the like. The glue may be applied by means of a syringe or the like through a hole made between the outer surface of the catheter body 12 and the central lumen 18. Such a hole may be formed, for example, by a needle or the like that punctures the outer wall 22 of the catheter body 12 and the stiffening tube 20 which is heated sufficiently to form a permanent hole. The glue is then introduced through the hole to the outer surface of the compression coil 56 and wicks around the outer circumference to form a glue joint about the entire circumference of the compression coil.

With reference to FIGS. 2A, 3B and 4B, the puller wire 42A extends into the first lumen 30 of the intermediate section 14. The puller wire 42A is anchored at its distal end to the tip electrode 37 within the third blind hole 73 in the plug 39. The puller wire 42B extends into the second lumen 32 of the intermediate section 14. The puller wire 42 is anchored at its distal end to the tip electrode 37 within the fourth blind hole 75 in the plug 39. The blind holes 73 and 75 are positioned in generally opposing positions along a diameter of the tip electrode 37 and the holes are generally aligned with the lumens 30 and 32, respectively, of the intermediate section 14 to provide bi-directional deflection in the intermediate and tip sections of the catheter. A method for anchoring the puller wires 42 within the tip electrode 37 is by crimping metal tubing 46 to the distal end of the puller wires 42 and soldering the metal tubing 46 inside the blind holes 73 and 75. Anchoring the puller wires 42 within the tip electrode 37 provides additional support, reducing the likelihood that the tip electrode 37 will fall off. Alternatively, the puller wires 42 can be attached to the side of the tubing 19 of the intermediate section 14. Within the first and second lumens 30 and 32 of the intermediate section 14, the puller wires 42 extend through a plastic, preferably Teflon®, sheath 81, which prevents the puller wires 42 from cutting into the wall of the intermediate section 14 when the intermediate section is deflected.

Longitudinal movement of the puller wire 42 relative to the catheter body 12, which results in deflection of the tip section 36, is accomplished by suitable manipulation of the control handle 16. Suitable control handles are described in U.S. Pat. No. 6,602,242, the entire disclosure of which is hereby incorporated by reference.

In the illustrated embodiment of FIGS. 4A, 4B and 4C, the tip section 36 carries an electromagnetic sensor 72. In particular, the electromagnetic sensor may be carried in the plastic housing 21, with its distal end anchored in a blind hole 79 formed in the plug 39. The electromagnetic sensor 72 is connected to an electromagnetic sensor cable 74, which extends through the third lumen 34 of the tip section 36, through the central lumen 18 of the catheter body 12, and into the control handle 16. The electromagnetic sensor cable 74 then extends out the proximal end of the control handle 16 within an umbilical cord 78 to a sensor control module 75 that houses a circuit board (not shown). Alternatively, the circuit board can be housed within the control handle 16, for example, as described in U.S. patent application Ser. No. 08/924,616, entitled "Steerable Direct Myocardial Revascularization Catheter", the disclosure of which is incorporated herein by reference. The electromagnetic sensor cable 74 comprises multiple wires encased within a plastic covered sheath. In the sensor control module 75, the wires of the electromagnetic sensor cable 74 are connected to the circuit board. The circuit board amplifies the signal received from the electromagnetic sensor 72 and transmits it to a computer in a form understandable by the computer by means of the sensor connector 77 at the proximal end of the sensor control module 75, as shown in FIG. 1. Because the catheter can be designed for single use only, the circuit board may contain an EPROM chip which shuts down the circuit board approximately 24 hours after the catheter has been used. This prevents the catheter, or at least the electromagnetic sensor, from being used twice. Suitable electromagnetic sensors for use with the present invention are described, for example, in U.S. Pat. Nos. 5,558,091, 5,443,489, 5,480,422, 5,546,951, 5,568, 809, and 5,391,199 and International Publication No. WO 95/02995, the disclosures of which are incorporated herein by reference. An electromagnetic mapping sensor 72 may have a length of from about 6 mm to about 7 mm and a diameter of about 1.3 mm.

In accordance with a feature of the present invention, the catheter 10 is adapted to facilitate optically-based real-time assessment of ablation tissue characteristics, including without limitation, lesion formation, depth of penetration of the lesion, cross-sectional area of the lesion, formation of char during ablation, recognition of char during ablation, differentiation of char from non-charred tissue, formation of coagulum around the ablation site, differentiation of coagulated from non-coagulated blood, differentiation of ablated from healthy tissue, tissue proximity, and recognition of steam formation in the tissue for prevention of steam pop. These assessments are accomplished by measuring the light intensity at one or more wavelengths that is recaptured at the catheter resulting from the light radiated from the catheter tip onto ablated tissue.

As shown in FIGS. 2B, 3A and 4A, an optical waveguide, e.g., a fiber optic cable 43E, is provided in the catheter to transport light energy to the tip section 36. In the disclosed embodiment, the fiber optic cable 43E is protectively housed in the catheter from the control handle 16 to the tip section 36. The cable 43E functions as a light transmitting cable in the tip section by transmitting light energy to the tip section 36 from an external and/or internal light source. It is understood by one of ordinary skill in the art that optical waveguides and fiber optic cables in general serve to transmit optical energy from one end to the other, although these are not exclusive.

Figure 6A:
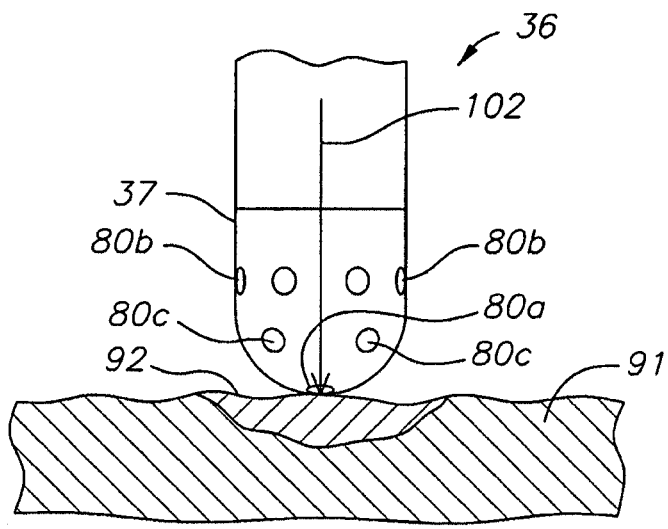
FIG. 6A is a side view of an embodiment of a tip section whose longitudinal axis is generally perpendicular to tissue surface.
Figure 6B:
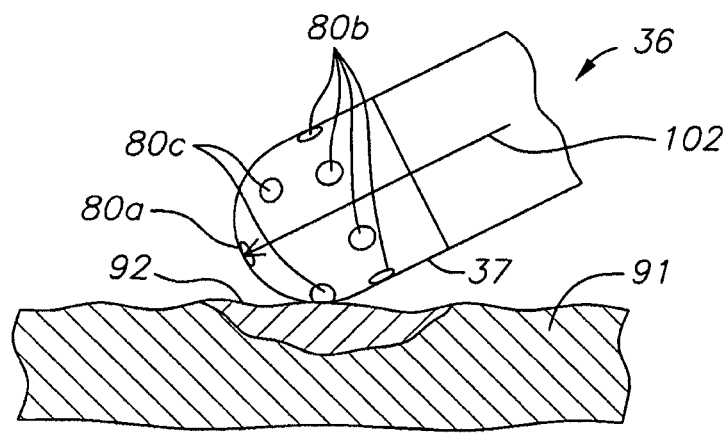
FIG. 6B is a side view of an embodiment of a tip section whose longitudinal axis is generally at an angle between zero and 90 to tissue surface.
Figure 6C:
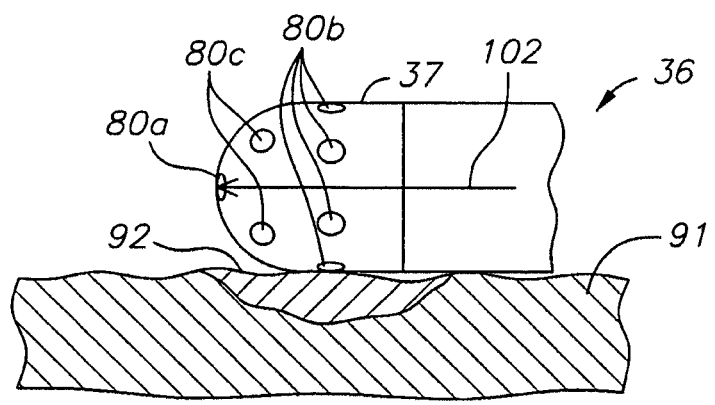
FIG. 6C is a side view of an embodiment of a tip section whose longitudinal axis is generally parallel to tissue surface.

Light from the fiber optic cable 43E enters a light reflection chamber 44 provided in the tip section 36 as shown in FIGS. 4A and 4B. In the disclosed embodiment, the shell 38 and the plug 39 of the tip electrode 37 are configured such that when assembled the light reflection chamber 44 is provided at the distal end of the tip electrode 37. An interior surface 47 of the chamber is defined by an interior surface of the shell 38 and a distal end of the plug 39, each of whose surfaces has been polished or otherwise prepared to specularly or diffusely scatter incidental light with minimum attenuation. The polished interior surface of the chamber serves to specularly scatter light throughout the chamber. Such specular scattering advantageously avoids "hot spots" in the tip electrode 37 and creates generally equal optical intensity (or optical flux defined in units of power per unit area) at every location in the chamber and hence generally uniform optical intensity throughout the chamber. With reference to FIGS. 6A-6C, the specularly scattered light in the chamber radiates tissue 91 at the treatment site by passing through openings 80 configured in the shell 38 of the tip electrode 37.

As lesion 92 forms in the tissue 91 from ablation carried out by the catheter 10 (or by another catheter), its characteristics are altered as understood by one of ordinary skill in the art. In particular, as the lesion is radiated, the radiation is scattered and/or reflected back toward the tip section 36, where such light having interacted or otherwise having been affected by the lesion bears qualitative and quantitative information about the lesion 92 as it returns to the chamber through the openings 80.

Upon return to the reflection chamber 44, most if not all of the light is again specularly scattered. With incidence on a receiving optical receiver, for example, a fiber optic cable 43R, provided in the chamber 44, the light bearing the qualitative and quantitative information is transmitted to an optical processing system as described below in further detail.

As shown in FIGS. 2B, 3A and 4A, the cables 43E and 43R are protectively housed along the length of the catheter. They extend through the tubing 18 of the catheter body 12, through the third lumen 34 of the intermediate section 14 and through passages 53 formed in the plug 39 of the tip electrode 37, with their distal ends anchored at or near the distal end of the plug 39. The passages 53 are generally aligned with the third lumen 34 of the intermediate section 14 to minimize stress on the cables 43E and 43R in their transition between the intermediate section 14 and the tip section 36.

The polished interior surface 47 of the chamber effectively scatters the light from the cable 43E throughout the chamber 44, and enables the collection of lesion optical data by the cable 43R despite the relative localized, stationary and off-axis dispositions of the distal ends of these cables. That is, such radiation and collection by the fiber optic cables are possible regardless of their positions in the chamber because of the isotropic scattering provided by the polished interior surface. This feature permits the tip section to be designed, manufactured or assembled with greater flexibility and adaptability. To further encourage isotropic scattering in the chamber, the shell 38 and the plug 39 may be configured to avoid linear alignment between the distal ends of the cables 43 and the openings 80.

Figure 7:
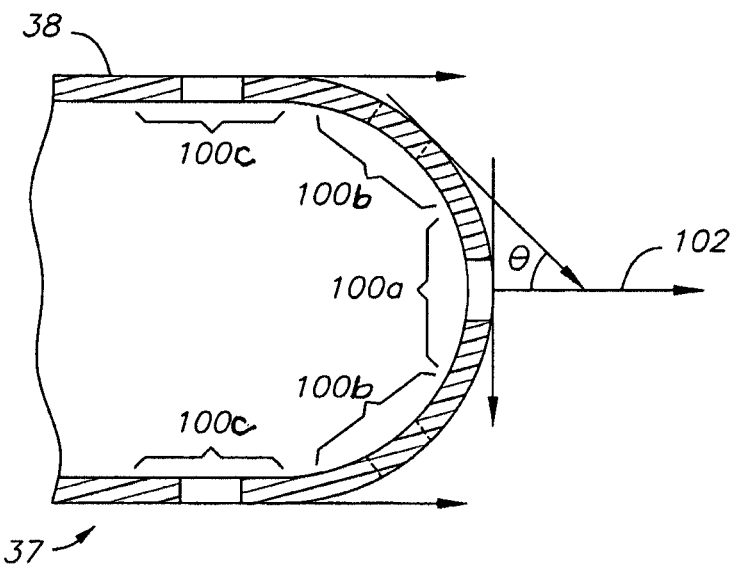
FIG. 7 is a side cross-section view of an embodiment of a shell of a tip electrode showing angled portions and openings.

In accordance with a feature of the present invention, the tip section 36 serves as a generally omni-directional optical radiator and collector. In the disclosed embodiment, the shell 38 of the tip electrode 37 is configured with portions 100 that provide different angles of orientation relative to a longitudinal axis 102 of the tip electrode. Accordingly, the tip section accomplishes effective radiation and collection of lesion optical data for nearly any angle of orientation between the catheter and the tissue of interest. With reference to FIG. 7, the shell 38 of the tip electrode 37 is configured with (i) a first or distal portion 100a whose surface is generally perpendicular to the axis 102, (ii) a second or radial portion 100b whose surface is at an angle $\theta$ relative to the axis, where the angle $\theta$ ranges between about zero and 90 degrees, preferably between about 20 and 70 degrees, and more preferably about 45 degrees, and (iii) a third or circumferential portion 100c whose surface is generally parallel to the axis. In the illustrated embodiment, the shell 38 is configured with a hollow dome design having a generally spherical, parabolic, or at least rounded convex distal portion to provide the sections 100 and yet be of an atraumatic design. With at least one if not more openings 80 configured in each of sections 100, light can exit and enter the chamber 44 from many different angles and directions.

Figure 5:
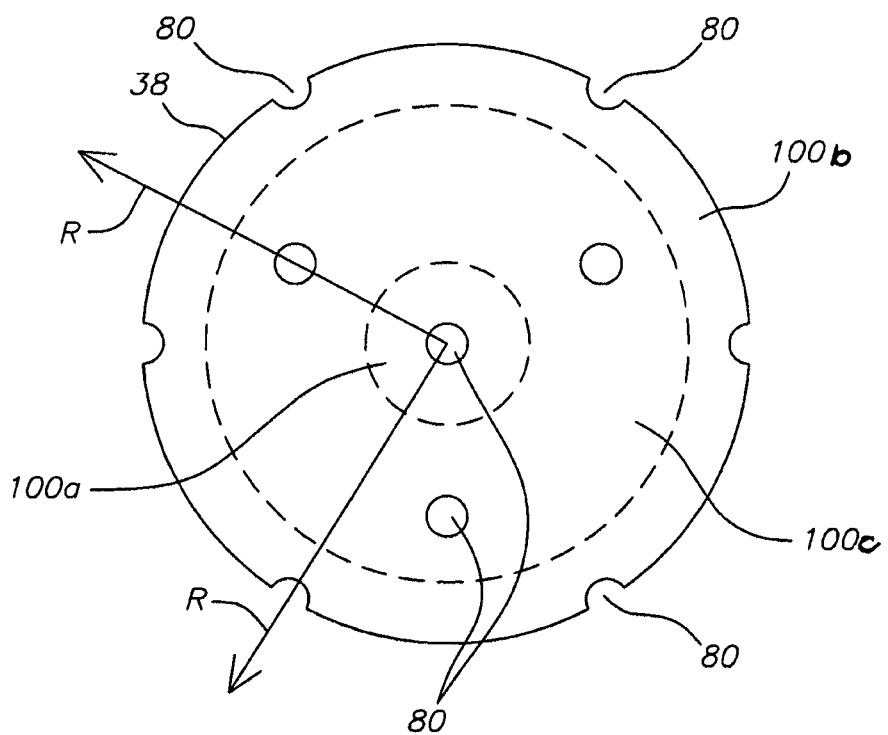
FIG. 5 is an end view of the distal end of an embodiment of a tip electrode showing angled portions and optical openings.

With reference to the illustrated embodiment of FIG. 5, the first portion 100a has a single opening 80 that is located on or near the distal most location of the electrode on the longitudinal axis 102 (or apex of the tip electrode), the second portion 100b has three openings 80 that are generally equi-angular from each other at about 120 degrees in circumference and at generally equi-distance from the apex, and the third portion 100c has six openings 80 that are generally equi-angular from each other at about 60 degrees in circumference and at generally equi-distance from the apex. Thus, in the illustrated embodiment, a total of ten openings are provided in the tip electrode 37. Moreover, it may be desirable that the openings of different sections are radially offset from each other for optimal radiation and capture of optical data as best shown in FIG. 5 (where no openings of adjacent sections 100b and 100c are aligned on any one radial line R). It is understood by one of ordinary skill in the art that the plurality and configuration of the portions 100 and the openings 80 may be varied as appropriate or desired. The size and dimensions of each portion may also be varied as appropriate or desired, as well as the shape of the openings, which can be round, ovular, square, polygonal, flat (slit), or any combination of these shapes.

Such variously angled portions 100 (and their corresponding openings 80) advantageously enable generally omni-directional emission and collection of radiation between the catheter and tissue. In FIG. 6A, the angle of orientation of the tip section 36 (generally defined by the longitudinal axis 102 of the tip electrode 37 to the surface of the lesion 92) is about 90 degrees, such that radiation of the lesion and collection of lesion optical data can be accomplished primarily through light passing through opening 80a in the first portion 100a, with perhaps contribution from the light passing through openings 80c in the second portion 100b. In FIG. 6B, the angle of orientation is about 30 degrees, such that radiation of the lesion 92 and collection of lesion optical data can be accomplished primarily through light passing through openings 80c in the second portion 100b, with perhaps contribution from light passing through opening 80a in the distal portion 100a and/or openings 80b in the third portion 100c. In FIG. 6C, the angle of orientation is about zero degrees, such that radiation of the lesion 92 and collection of lesion optical data can be accomplished primarily through light passing through openings 80b in the third portion 100c, with perhaps contribution from light passing through openings 80c of the second portion 100b.

It is understood that the fiber optic cables 43E and 43R may be any suitable optical wave guide wherein light introduced at one of the cable is guided to the other end of the cable with minimal loss. Each of the cables 43E and 43R may be a single fiber optic cable or fiber bundles. They may be single mode (also known as mono-mode or uni-mode), multi-mode (with step index or graded index) or plastic optical fiber (POF), depending on a variety of factors, including but not limited to transmission rate, bandwidth of transmission, spectral width of transmission, distance of transmission, diameter of cable, cost, optical signal distortion tolerance and signal attenuation, etc.

To keep the openings 80 generally free from obstruction from blood or other bodily fluids and tissue encountered by the tip electrode 37, the tip electrode is irrigated with fluid, e.g., saline, that is fed into the chamber 44 by an irrigation tube segment 48 that extends from the distal end of the fourth lumen 35 of the intermediate section 14, through the plastic housing 21 and passage 95 in the plug 39. The distal end of the segment 48 is anchored in the passage 95 and the proximal end is anchored in the fourth lumen 35 by polyurethane glue or the like. The passage 95 is generally aligned with the fourth lumen 35 of the intermediate section 14. The segment 48, like the puller wires 42, provides additional support for the tip electrode. The irrigation tube segment 48 is in communication with a proximal infusion tube segment 88 that extends through the central lumen 18 of the catheter body 12 and terminates in the proximal end of the fourth lumen 35 of the intermediate section 14. The distal end of the proximal infusion tube segment 88 is anchored in the fourth lumen 35 by polyurethane glue or the like. The proximal end of the first infusion tube segment 88 extends through the control handle 16 and terminates in a luer hub 90 (FIG. 1) or the like at a location proximal to the control handle. In practice, fluid may be injected by a pump (not shown) into the infusion tube segment 88 through the luer hub 90, and flows through the segment 88, through the fourth lumen 35, through the infusion tube segment 48, into the chamber 44 in the tip electrode 37, and out the openings 80. The infusion tube segments may be made of any suitable material, and is preferably made of polyimide tubing. A suitable infusion tube segment has an outer diameter of from about 0.32 inch to about 0.036 inch and an inner diameter of from about 0.28 inch to about 0.032 inch.

In accordance with a feature of the present invention, the pump maintains the fluid at a positive pressure differential relative to outside the chamber 44 so as to provide a constant unimpeded flow or seepage of fluid outwardly from the chamber 44 which continuously flushes the openings 80 and minimizes obstruction so light can freely pass through for the aforementioned radiation and collection purposes. In addition to the above, the irrigation adaptation of the catheter 10 may serve other typical functions such as cooling the tip electrode and/or the ablation site and increasing conduction for deeper and larger lesions.

Figure 8:
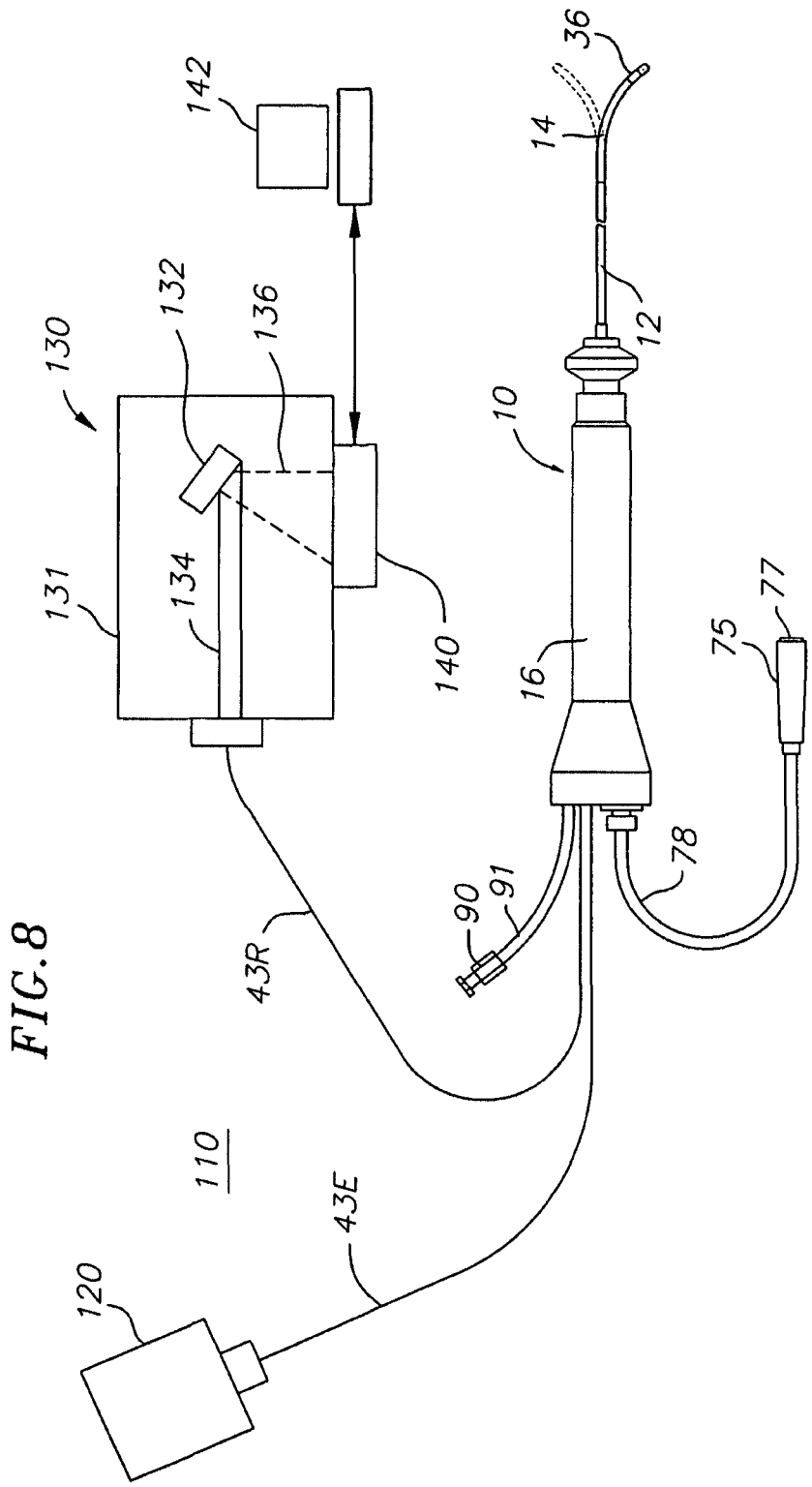
FIG. 8 is a schematic drawing showing components of an embodiment of an optical processing system for use with the catheter of the present invention.

With reference to FIG. 8, an optical processing system 110 for optically evaluating ablation tissue using the catheter 10 is illustrated. A light source 120 supplies a broadband (white; multiple wavelengths) light and/or laser light (single wavelength) radiation to the tip section 36 of the catheter 10 via the emitting cable 43E, and light bearing lesion qualitative information from the tip section is transmitted by the receiving cable 43R to a detection component 130. The detection component may comprise, for example, a wavelength selective element 131 that disperses the collected light into constituent wavelengths, and a quantification apparatus 140. The at least one wavelength selective element 131 includes optics 132, as are known in the art, for example, a system of lenses, mirrors and/or prisms, for receiving incident light 34 and splitting it into desired components 136 that are transmitted into the quantification apparatus 140.

The quantification apparatus 140 translates measured light intensities into an electrical signal that can be processed with a computer 142 and displayed graphically to an operator of the catheter 10. The quantification apparatus 140 may comprise a charged coupled device (CCD) for simultaneous detection and quantification of these light intensities. Alternatively, a number of different light sensors, including photodiodes, photomultipliers or complementary metal oxide semiconductor (CMOS) detectors may be used in place of the CCD converter. Information is transmitted from the quantification device 140 to the computer 142 where a graphical display or other information is generated regarding parameters of the lesion. A suitable system for use with the catheter 10 is described in U.S. application Ser. No. 11/281,179 entitled Apparatus for Real Time Evaluation of Tissue Ablation, and Ser. No. 11/281,853 entitled Method for Real Time Evaluation of Tissue Ablation, the entire disclosures of which are hereby incorporated by reference.

Figure 9:
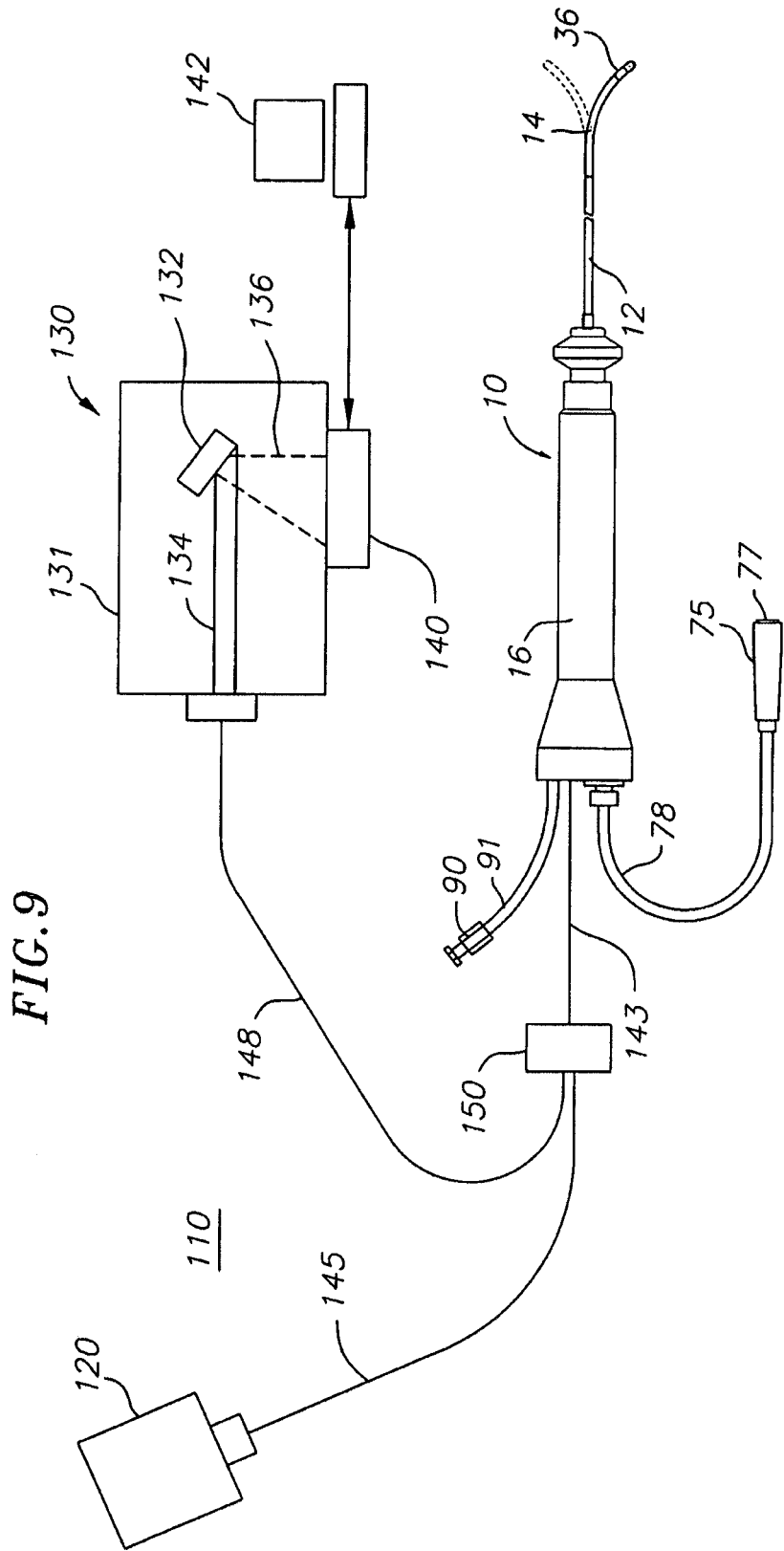
FIG. 9 is a schematic drawing showing components of an alternative embodiment of an optical processing system for use with the catheter of the present invention.

In an alternative embodiment as illustrated in FIG. 9, the fiber optic cables 43E and 43R are replaced by a single fiber optic cable 143 such that light to and from the chamber 44 travel through the cable 143 in opposite directions. A beam splitter 150 or the like is provided to split the optical path such that light from the light source 120 travels to the catheter through an optical waveguide, e.g., fiber optic 145, through the beamsplitter and through the cable 143, and light from the chamber 44 travels through the cable 143, the beamsplitter 150 and through an optical waveguide, e.g., fiber optic 148, to the detection component 130 and quantification apparatus 140.

In another alternative embodiment as illustrated in FIG. 10, a lens 155 is positioned over the fiber optical cables 43E and 43C or optical cable 143 to diffusely scatter the light emitted and collected by the cables, in addition to the polished interior surface of the chamber 44. In this illustrated embodiment, the tip electrode 37 is attached to the plastic housing 21 by creating a circumferential notch 37 in the distal end of the housing 21, placing the proximal end of the tip electrode on the distal end of the housing 21, and filling the notch 37 with glue. It is understood by one of ordinary skill in the art that the notch 37 may be formed in the proximal end of the tip electrode to accomplish attachment to the housing 21 and that a variety different means and structures can be used accomplish this attachment.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter, comprising:
a catheter body;
a tip section distal the catheter body adapted for ablating tissue, the tip section having a light diffusion chamber adapted to diffusively scatter light, the light diffusion chamber having at least three openings, a distal end of the tip section comprising at least a first portion having a surface generally perpendicular to a longitudinal axis of the tip section, a second portion having a surface at an angle relative to the longitudinal axis of the tip section, and a third portion having a generally circumferential surface that is generally parallel to the longitudinal axis of the tip section, wherein each of the first, second and third portions of the tip section carries at least one of the openings of the light diffusion chamber and the at least one of the openings of the second portion is radially offset from the at least one of the openings of the third portion.

2. A catheter of claim 1, further comprising irrigation means for flushing the openings with fluid.

3. A catheter of claim 1, further comprising at least a first optical waveguide to deliver light energy to the chamber and at least a second optical waveguide to receive light from the chamber.

4. A catheter of claim 1, wherein the chamber is formed within a tip electrode of the tip section.

5. A catheter of claim 3, wherein the first and second optical waveguides extend through the catheter body and a proximal portion of the tip section.

6. A catheter of claim 1, wherein an interior surface of the chamber specularly and/or diffusely scatters the light.

7. A catheter of claim 1, wherein an interior surface of the chamber is polished to specularly and/or diffusely scatter the light.

8. A catheter adapted to ablate tissue, comprising: a catheter body;
a tip section distal the catheter body adapted for ablating tissue, the tip section having a light diffusion chamber with at least three openings to allow light in the chamber to radiate the tissue and return to the chamber, a distal end of the tip section comprising at least a first portion having a surface generally perpendicular to a longitudinal axis of the tip section, a second portion having a surface at an angle relative to the longitudinal axis of the tip section, and a third portion having a generally circumferential surface that is generally parallel to the longitudinal axis of the tip section, wherein each of the first, second and third portions of the tip section carries at least one of the openings of the light diffusion chamber and the at least one of the openings of the second portion is radially offset from the at least one of the openings of the third portion; and
irrigation means for flushing the at least three openings with fluid;
wherein the light returning to the light diffusion chamber from the tissue carries information regarding a tissue parameter.

9. A catheter of claim 8, wherein the at least three openings in the first, second and third portions of the tip section provide different angles of incidence of the light on the tissue.

10. A catheter of claim 8, wherein the first second and third portions of the tip section accommodate a different range of angles between the catheter tip section and the tissue.

11. A catheter of claim 8, wherein the angle of the second portion ranges between about zero and 90 degrees relative to the longitudinal axis of the tip section.

12. A catheter of claim 11, wherein the angle of the second portion ranges between about 20 and 70 degrees.

13. A catheter of claim 11, wherein the angle of the second portion is about 45 degrees.

14. A catheter of claim 11, wherein the first portion has one passage opening, the second portion has three openings, and the third portion has six openings.

15. A catheter of claim 8, further comprising a first optical guide to transmit light to the chamber; and a second optical guide to collect light in the chamber.

16. A catheter of claim 8, further comprising a deflectable intermediate section between the catheter body and the tip section.

17. A catheter according to claim 16, wherein a tubing of the intermediate section is more flexible than the catheter body.

18. A catheter according to claim 16, further comprising means for deflecting the intermediate section.

19. A catheter of claim 8, wherein the tip section includes a tip electrode having a shell and a plug.

20. A catheter of claim 19, wherein the tip electrode is made of thermally and electrically conductive material.

21. A catheter of claim 8, wherein the tissue parameter includes at least one of lesion formation, depth of penetration of lesion, cross-sectional area of lesion, temperature of the tissue, formation of char during ablation, recognition of char during ablation, recognition of char from non-charred tissue, formation of coagulum around the ablation site, differentiation of coagulated from non-coagulated blood, differentiation of ablated from healthy tissue, tissue proximity, and recognition of steam formation in the tissue for prevention of steam pop.

22. A catheter of claim 8, wherein the fluid in the chamber is maintained at a positive pressure differential relative to outside the tip section for generally continuous flushing of the openings.

23. A catheter of claim 8, wherein the light is specularly and/or diffusively scattered in the chamber before exiting the chamber toward the tissue.

24. A catheter of claim 8, wherein the light returning to the chamber is specularly and/or diffusively scattered in the chamber.

25. A catheter of claim 8, wherein the catheter is adapted to provide optical data of the tissue for angles between a longitudinal axis of the tip section and the tissue ranging between generally zero and 90 degrees.

26. A catheter of claim 8, further comprising at least one optical fiber cable whose distal end is in communication with the chamber.

27. A catheter of claim 26, wherein the at least one optical fiber cable is adapted for two-way transmission of the light.

28. A catheter of claim 8, further comprising an electromagnetic location sensor carried at or near the tip section for producing electrical signals indicative of a location of the electromagnetic location sensor.

29. A catheter of claim 8, further comprising a temperature sensor.

30. A catheter of claim 8, wherein the tip section includes a tip electrode adapted for RF energy ablation.

31. A catheter adapted to ablate tissue, comprising:
a catheter body;
a tip section distal the catheter body adapted for ablating tissue, the tip section having a tip electrode with a light diffusion chamber with openings to allow light energy in the chamber to radiate the tissue and return to the chamber, the electrode comprising at least a first portion having a surface generally perpendicular to a longitudinal axis of the tip section, a second portion having a surface at an angle $\theta$ ranging from about 0 to about 90° relative to the longitudinal axis of the tip section, and a third portion having a generally circumferential surface that is generally parallel to the longitudinal axis of the tip section, wherein each of the first, second and third portions of the tip section carries at least one of the openings of the light diffusion chamber and the at least one of the openings of the second portion is radially offset from the at least one of the openings of the third portion; and
irrigation means for flushing the openings with fluid.

32. A catheter of claim 31, wherein the angle of the second portion is between about 20 and 70 degrees.

33. A catheter of claim 31, wherein the angle of the second portion is about 45 degrees.

* * * * *